US012661053B2

(12) United States Patent
Chen et al.

(10) Patent No.: US 12,661,053 B2
(45) Date of Patent: Jun. 23, 2026

(54) ELECTROCARDIOGRAM ("ECG") SIGNAL ANALYSIS AND S-T SEGMENT MEASUREMENT

(71) Applicant: DRÄGERWERK AG & CO. KGAA, Lübeck (DE)

(72) Inventors: Yu Chen, Andover, MA (US); Haisheng Lu, Andover, MA (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 143 days.

(21) Appl. No.: 18/736,224

(22) Filed: Jun. 6, 2024

(65) Prior Publication Data

US 2024/0415441 A1      Dec. 19, 2024

Related U.S. Application Data

(60) Provisional application No. 63/521,564, filed on Jun. 16, 2023.

(51) Int. Cl.
*A61B 5/358*        (2021.01)
*A61B 5/00*        (2006.01)
(52) U.S. Cl.
CPC ............ *A61B 5/358* (2021.01); *A61B 5/7203* (2013.01)
(58) Field of Classification Search
None
See application file for complete search history.

(56) References Cited

U.S. PATENT DOCUMENTS

| | | | | |
|---|---|---|---|---|
| 3,858,034 A | * | 12/1974 | Anderson .............. | A61B 5/316 600/517 |
| 5,704,365 A | * | 1/1998 | Albrecht .............. | A61B 5/4884 128/901 |
| 8,209,002 B2 | * | 6/2012 | Vajdic ..................... | A61B 5/36 600/512 |
| 10,188,305 B2 | * | 1/2019 | Zhang .................... | A61B 5/349 |
| 12,521,071 B1 | * | 1/2026 | Fischell ................. | A61B 5/686 |
| 2003/0069512 A1 | * | 4/2003 | Kaiser ................... | A61B 5/349 600/516 |
| 2013/0281816 A1 | * | 10/2013 | Strauss ................ | A61B 5/0006 600/386 |
| 2015/0272462 A1 | * | 10/2015 | Nearing ............... | A61B 5/7246 600/512 |
| 2017/0000367 A1 | * | 1/2017 | Grunwald ......... | A61M 25/0026 |
| 2019/0365268 A1 | * | 12/2019 | Li .......................... | A61B 5/366 |

* cited by examiner

*Primary Examiner* — James B Hull
(74) *Attorney, Agent, or Firm* — Nolte Lackenbach Siegel

(57)        ABSTRACT

A method of processing of electrocardiogram ("ECG") signals from at least one ECG lead connected to a patient includes computing an average beat from a plurality of beats occurring during a predetermined averaging interval. An onset point, isoelectric point, and a J-point of the average beat is computed to establish an S-T segment of the average beat. The isoelectric point and the J-point of the average beat are used to determine an S-T segment for each beat of the averaging interval, and the average of the S-T segments of each beat is computed and averaged with the S-T segment of the average beat.

20 Claims, 7 Drawing Sheets

100 —

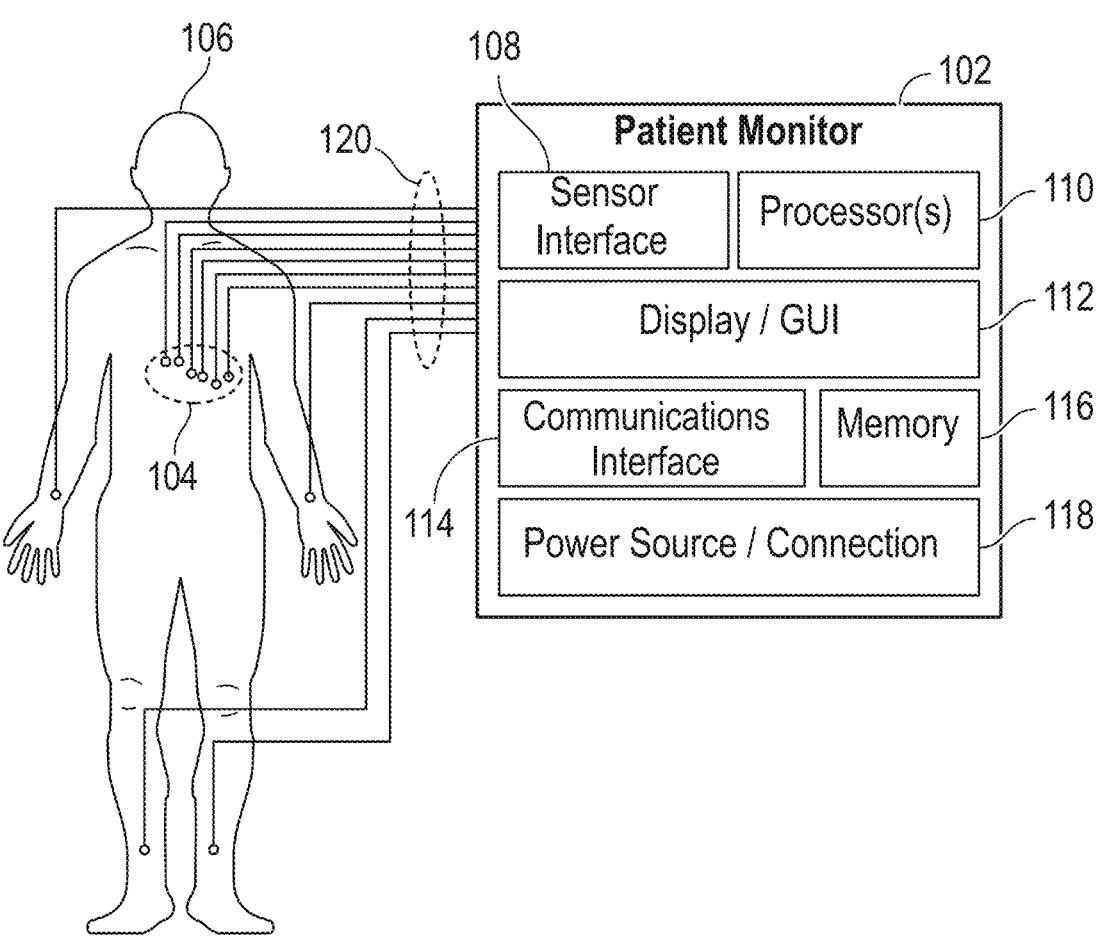
FIG. 1

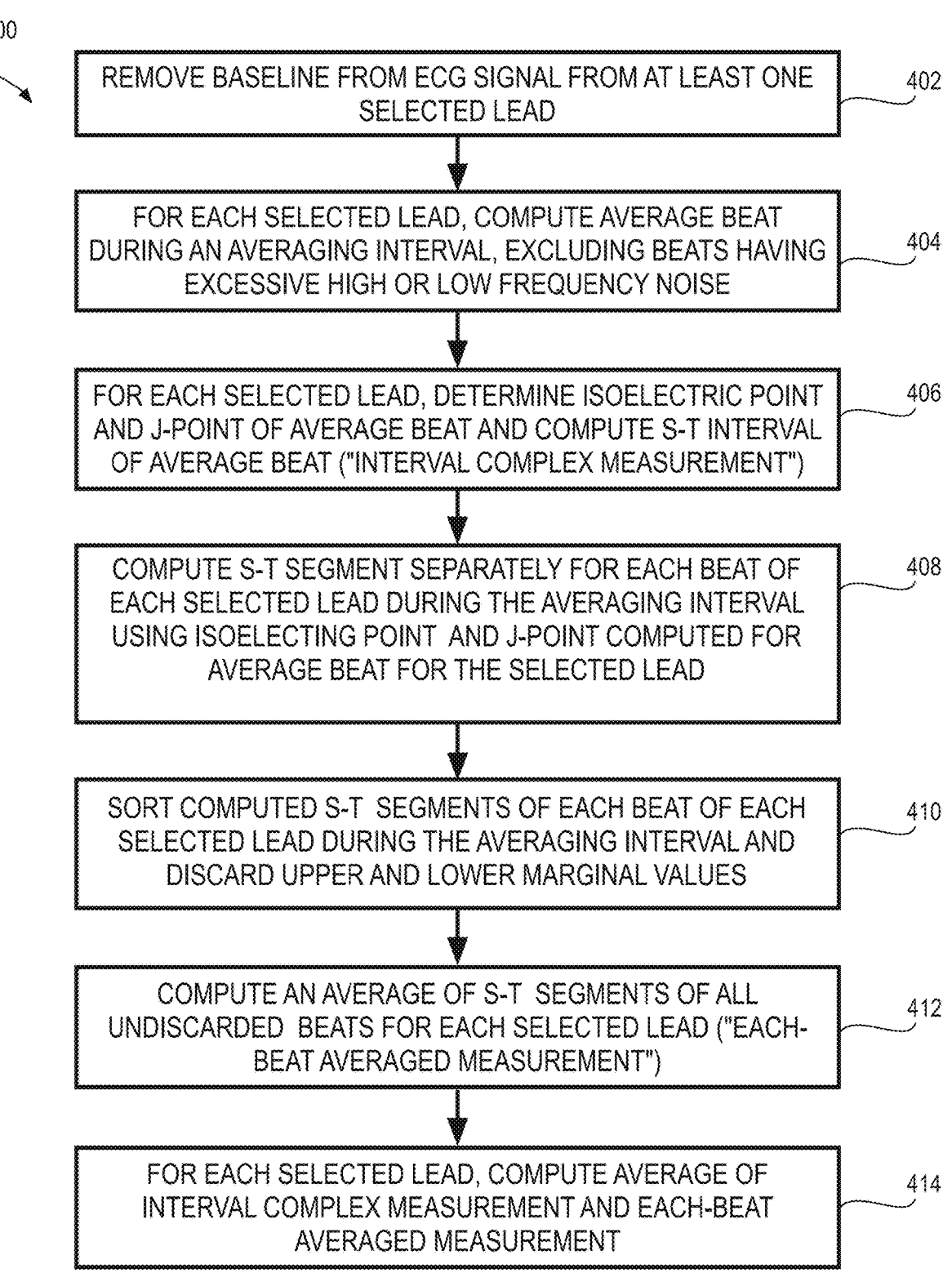

400

REMOVE BASELINE FROM ECG SIGNAL FROM AT LEAST ONE SELECTED LEAD —— 402

FOR EACH SELECTED LEAD, COMPUTE AVERAGE BEAT DURING AN AVERAGING INTERVAL, EXCLUDING BEATS HAVING EXCESSIVE HIGH OR LOW FREQUENCY NOISE —— 404

FOR EACH SELECTED LEAD, DETERMINE ISOELECTRIC POINT AND J-POINT OF AVERAGE BEAT AND COMPUTE S-T INTERVAL OF AVERAGE BEAT ("INTERVAL COMPLEX MEASUREMENT") —— 406

COMPUTE S-T SEGMENT SEPARATELY FOR EACH BEAT OF EACH SELECTED LEAD DURING THE AVERAGING INTERVAL USING ISOELECTING POINT AND J-POINT COMPUTED FOR AVERAGE BEAT FOR THE SELECTED LEAD —— 408

SORT COMPUTED S-T SEGMENTS OF EACH BEAT OF EACH SELECTED LEAD DURING THE AVERAGING INTERVAL AND DISCARD UPPER AND LOWER MARGINAL VALUES —— 410

COMPUTE AN AVERAGE OF S-T SEGMENTS OF ALL UNDISCARDED BEATS FOR EACH SELECTED LEAD ("EACH-BEAT AVERAGED MEASUREMENT") —— 412

FOR EACH SELECTED LEAD, COMPUTE AVERAGE OF INTERVAL COMPLEX MEASUREMENT AND EACH-BEAT AVERAGED MEASUREMENT —— 414

FIG. 4

ELECTROCARDIOGRAM ("ECG") SIGNAL ANALYSIS AND S-T SEGMENT MEASUREMENT

CROSS-REFERENCE TO RELATED APPLICATION

This application claims priority to U.S. Provisional Patent Application No. 63/521,564 filed Jun. 16, 2023, the contents of which being incorporated herein by reference.

BACKGROUND

The present disclosure relates generally to the field of electrocardiogram ("ECG") signal analysis. More particularly, the present disclosure relates to ECG waveform analysis including artifact detection and rejection, and cardiac signal segment measurements.

Electrocardiogram systems are commonly used to monitor patients' heart conditions as well to detect or predict cardiac events and conditions. In clinical settings, ECG signals representative of a patient's condition are captured in waveforms and analyzed by physiological monitoring devices. The physiological monitoring devices identify systolic segments of the captured waveforms, such as QRS-complexes, P-Q segments, S-T segments, and the like. These systolic segments reflect the progression of electrical signals in the heart and corresponding to the depolarization of the right and left ventricles and the contraction of cardiac muscles. For a normal sinus rhythm, an R-wave (a sharp upward deflection) in the QRS-complex with a large amplitude and a small width, is suitable for measuring heart rate and other cardiac conditions. Physiological monitoring devices further classify the detected ECG waveforms into different types, based on features extracted from the morphology of various systolic segment.

In clinical settings, noise contamination caused by artifact signals may adversely impact the precision and accuracy of ECG signal analysis including identification of various systolic segments and subsequent beat classification. For example, noise contamination may impact the accuracy of algorithms designed to detect several cardiac pathologies such as arrhythmias. As a result, a high rate of false arrhythmia alarms may lead to alarm fatigue, where clinicians may be potentially desensitized to frequent invalid or nonactionable alarms and therefore, silencing the alarms with a risk of missing genuine and critical alarms.

A variety of sources may cause artifact signals, including physiological artifacts caused by patients and non-physiological artifacts caused by electric circuitry in the physiological monitoring devices and/or other devices in the clinical environment. Thus, it is important for physiological monitoring devices to accurately detect artifact signals, identify and analyze the corrupted segments of ECG signals contaminated by artifacts.

SUMMARY

There exists a need for improved detection and analysis of ECG signals, for the physiological monitoring device to identify artifact signals and accordingly, analyze ECG signals in real-time even in the presence of artifacts. There also exists a need for identifying and analyzing systolic segments in real-time in the presence of noise, for heart rate calculation and beat classification, as well as alarm generation.

To resolve or mitigate at least one or more of the above problems and potentially other present or future problems, one aspect of the present disclosure relates to an apparatus for analyzing ECG signals obtained from a patient monitor including one or more ECG leads coupled to the patient.

The apparatus may include one or more processors configured by machine-readable instructions. The processor(s) may be configured to select a plurality of sample points from in the plurality of sample signals, extract a plurality of features from the selected plurality of sample points and generate a probability of the existence of the artifact signals in the plurality of sample signals, by applying a transformation process to at least two of the plurality of features. The processor(s) may further be configured to apply an algorithm to one or more signals to reliably and accurately detect one or more systolic segments of the sensed ECG signals.

One or more examples in the present disclosure provide but are not limited to the following advantages. Note that not all embodiments will necessarily manifest all of these advantages. Furthermore, to the extent that one or more embodiments manifest one or more of the advantages, not all embodiments will manifest such advantages to the same extent or degree.

A variety of artifact signals that cause disturbances in ECG monitoring can be detected in real-time. For example, the embodiments in the present disclosure are capable of detecting physiological artifacts caused by patient motion, including motions associated with the patient's medical conditions (e.g., tremors, shivering) and regular muscular activities (e.g., brushing, combing). Additionally, the embodiments in the present disclosure are capable of detecting non-physiological artifacts including electromagnetic interference caused by physiological monitoring systems or other electrical devices in the clinical environment, as well as artifacts caused by cable and/or electrode malfunction. Note that not all embodiments will necessarily exhibit all these advantages nor will they exhibit them to the same degree. Thus, the embodiments in the present disclosure prevent artifact signals from being falsely identified as part of a QRS-complex, thereby increasing the accuracy in QRS-complex identification and classification, as well as the accuracy in heart rate calculation and alarm generation.

On the other hand, when a patient has certain medical conditions, the morphologies of the monitored ECG waveforms can be complex or irregular, and thus, difficult to differentiate from artifact signals. The examples in the present disclosure provide validation processes for identified artifact signals, thereby reducing the false-positive rate. With the complex or irregular ECG waveforms being accurately identified rather than treated as artifacts, the examples in the present disclosure are capable of analyzing different types of ECG waveforms accurately and generating alarms. Thus, clinical providers can promptly identify the medical conditions of the patient and provide treatment as needed, thereby improving clinical workflows.

The above presents a simplified summary in order to provide a basic understanding of some aspects of what is claimed below. This summary is not an exhaustive overview of the claimed subject matter. It is not intended to identify key or critical elements of the disclosure or to delineate the scope of the claims. Its sole purpose is to present some concepts in a simplified form as a prelude to the more detailed description that is discussed later.

BRIEF DESCRIPTION OF THE DRAWINGS

In the drawings, like reference numbers generally indicate identical, functionally similar, and/or structurally similar elements.

FIG. 1 illustrates a patient monitoring system according to one or more examples;

FIG. 4 is a flow diagram illustrating a method S-T segment measurement according to one or more examples;

Figure 2:
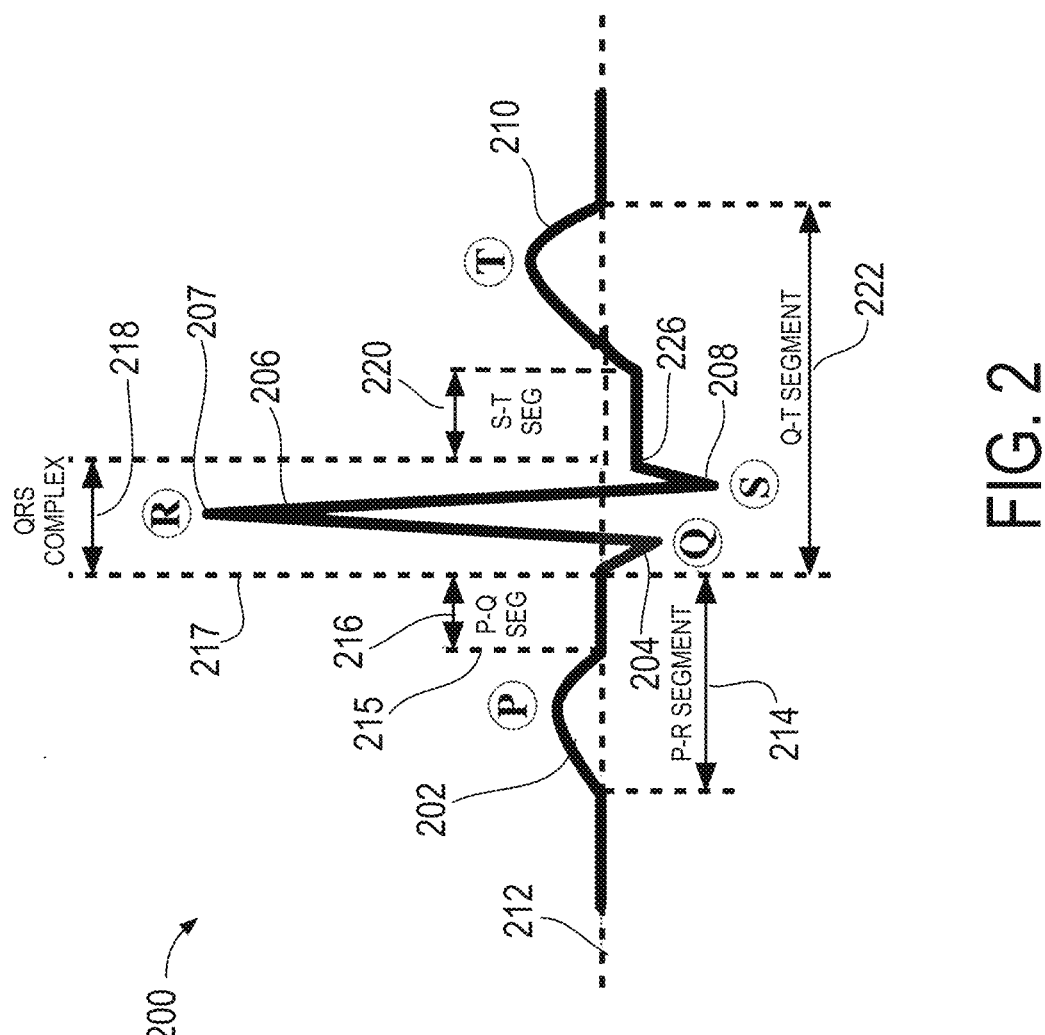
FIG. 2 is a schematic representation of a normal sinus rhythm ECG wave illustrating selected characteristics thereof.

While the disclosed subject matter is susceptible to various modifications and alternative forms, the drawings illustrate specific implementations described in detail by way of example. It should be understood, however, that the description herein of specific examples is not intended to limit that which is claimed to the particular forms disclosed, but on the contrary, the intention is to cover all modifications, equivalents, and alternatives falling within the spirit and scope of the appended claims.

DETAILED DESCRIPTION

Illustrative examples of the subject matter claimed below are disclosed. In the interest of clarity, not all features of an actual implementation are described for every example in this specification. It will be appreciated that in the development of any such actual implementation, numerous implementation-specific decisions may be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The expressions such as "include" and "may include" which may be used in the present disclosure denote the presence of the disclosed functions, operations, and constituent elements, and do not limit the presence of one or more additional functions, operations, and constituent elements. In the present disclosure, terms such as "include" and/or "have", may be construed to denote a certain characteristic, number, operation, constituent element, component or a combination thereof, but should not be construed to exclude the existence of or a possibility of the addition of one or more other characteristics, numbers, operations, constituent elements, components or combinations thereof.

As used herein, the article "a" is intended to have its ordinary meaning in the patent arts, namely "one or more." Herein, the term "about" when applied to a value generally means within the tolerance range of the equipment used to produce the value, or in some examples, means plus or minus 10%, or plus or minus 5%, or plus or minus 1%, unless otherwise expressly specified. Further, herein the term "substantially" as used herein means a majority, or almost all, or all, or an amount with a range of about 51% to about 100%, for example. Moreover, examples herein are intended to be illustrative only and are presented for discussion purposes and not by way of limitation.

As used herein, to "provide" an item means to have possession of and/or control over the item. This may include, for example, forming (or assembling) some or all of the item from its constituent materials and/or, obtaining possession of and/or control over an already-formed item.

Unless otherwise defined, all terms including technical and/or scientific terms used herein have the same meaning as commonly understood by one of ordinary skill in the art to which the present disclosure pertains. In addition, unless otherwise defined, all terms defined in generally used dictionaries may not be overly interpreted. In the following, details are set forth to provide a more thorough explanation of the embodiments. However, it will be apparent to those skilled in the art that embodiments may be practiced without these specific details. In other instances, well-known structures and devices are shown in block diagram form or in a schematic view rather than in detail in order to avoid obscuring the embodiments. In addition, features of the different embodiments described hereinafter may be combined with each other, unless specifically noted otherwise. For example, variations or modifications described with respect to one of the embodiments may also be applicable to other embodiments unless noted to the contrary.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

A sensor refers to a component which converts a physical quantity to be measured to an electric signal, for example, a current signal or a voltage signal. The physical quantity may for example comprise electromagnetic radiation (e.g., photons of infrared or visible light), a magnetic field, an electric field, a pressure, a force, a temperature, a current, or a voltage, but is not limited thereto.

ECG signal processing, as used herein, refers to, without limitation manipulating an analog signal in such a way that the signal meets the requirements of a next stage for further processing. ECG signal processing may include converting between analog and digital realms (e.g., via an analog-to-digital or digital-to-analog converter), amplification, filtering, converting, biasing, range matching, isolation and any other processes required to make a sensor output suitable for processing.

Turning now to the drawings, FIG. 1 shows a physiological monitoring system 100 according to one or more examples. As shown in FIG. 1, the system 100 includes a patient monitor 102 (e.g., a physiological monitoring device) capable of receiving physiological data from various sensors 104 connected to a patient 106. In this example, sensors 104 comprise ECG electrodes affixed to the skin of patient 106.

In general, it is contemplated by the present disclosure that patient monitor 102 includes electronic components and/or electronic computing devices operable to receive, transmit, process, store, and/or manage patient data and information associated performing the functions of the system as described herein, which encompasses any suitable processing device adapted to perform computing tasks consistent with the execution of computer-readable instructions stored in a memory or a computer-readable recording medium.

Further, any, all, or some of the computing devices in patient monitor 102 may be adapted to execute any operating system, including Linux®, UNIX®, Windows Server®, etc., as well as virtual machines adapted to virtualize execution of a particular operating system, including customized and proprietary operating systems. Patient monitor 102 may be further equipped with components to facilitate communication with other computing devices over one or more network connections, which may include connections to local and wide area networks, wireless and wired networks, public and private networks, and any other communication network enabling communication in the system.

As shown in FIG. 1, patient monitor 102 may be, for example, a patient monitor implemented to monitor various physiological parameters of patient 106 via sensors 104. Patient monitor 102 may include a sensor interface 108, one or more processors 110, a display/graphical user interface ("GUI") 112, a communications interface 114, a memory 116, and a power source (or power connection) 118. Sensor interface 108 may be implemented in hardware or combination of hardware and software and is used to connect via wired and/or wireless connections to sensors 104 for gathering physiological data from the patient 106. As noted, sensors 104 in the present example are ECG electrodes affixed to the skin of patient 106. A plurality of conductive leads 120, comprising a plurality of conductive cables, are provided for coupling sensors 104 to sensor interface 108. In one or more examples, conductive leads 120 comprise a plurality of ECG cables.

The data signals from the sensors 104 may include, for example, sensor data related to an ECG. The one or more processors 110 may be used for controlling the general operations of patient monitor 102, as well as processing sensor data received by sensor interface 108. The one or more processors 110 may be, but are not limited to, a central processing unit ("CPU"), a hardware microprocessor, a multi-core processor, a single core processor, a field programmable gate array ("FPGA"), a microcontroller, an application specific integrated circuit ("ASIC"), a digital signal processor ("DSP"), or other similar processing device capable of executing any type of instructions, algorithms, or software for controlling the operation and performing the functions of patient monitor 102. In some embodiments, the one or more processors 110 may comprise a processor chipset including, for example and without limitation, one or more co-processors.

Display/GUI 112 may be configured to display various patient data, sensor data, and hospital or patient care information, and includes a user interface implemented for allowing interaction and communication between a user and patient monitor 102. Display/GUI 112 may include a keyboard (not shown) and/or pointing or tracking device (not shown), as well as a display, such as a liquid crystal display ("LCD"), cathode ray tube ("CRT") display, thin film transistor ("TFT") display, light-emitting diode ("LED") display, high definition ("HD") display, or other similar display device that may include touch screen capabilities. Display/GUI 112 may provide a means for inputting instructions or information directly to the patient monitor 102. The patient information displayed may, for example, relate to the measured physiological parameters of patient 106 (e.g., ECG readings).

Communications interface 114 may enable patient monitor 102 to directly or indirectly (via, for example, a monitor mount) communicate with one or more computing networks and devices, workstations, consoles, computers, monitoring equipment, alert systems, and/or mobile devices (e.g., a mobile phone, tablet, or other hand-held display device). Communications interface 114 may include various network cards, interfaces, communication channels, cloud, antennas, and/or circuitry to enable wired and wireless communications with such computing networks and devices. Communications interface 114 may be used to implement, for example, a Bluetooth® connection, a cellular network connection, and/or a WiFi® connection with such computing networks and devices. Example wireless communication connections implemented using the communication interface 6 include wireless connections that operate in accordance with, but are not limited to, IEEE802.11 protocol, a Radio Frequency For Consumer Electronics ("RF4CE") protocol, and/or IEEE802.15.4 protocol (e.g., ZigBee® protocol). In essence, any wireless communication protocol may be used.

Additionally, communications interface 114 may enable direct (i.e., device-to-device) communications (e.g., messaging, signal exchange, etc.) such as from a monitor mount to patient monitor 102 using, for example, a universal serial bus ("USB") connection or other communication protocol interface. The communication interface 6 may also enable direct device-to-device connection to other devices such as to a tablet, computer, or similar electronic device; or to an external storage device or memory.

Memory 116 may be a single memory device or one or more memory devices at one or more memory locations that may include, without limitation, one or more of a random-access memory ("RAM"), a memory buffer, a hard drive, a database, an erasable programmable read only memory ("EPROM"), an electrically erasable programmable read only memory ("EEPROM"), a read only memory ("ROM"), a flash memory, hard disk, various layers of memory hierarchy, or any other non-transitory computer readable medium. Memory 116 may be used to store any type of instructions and patient data associated with algorithms, processes, or operations for controlling the general functions and operations of patient monitor 102.

Power source 118 may include a self-contained power source such as a battery pack and/or include an interface to be powered through an electrical outlet (either directly or by way of a monitor mount). Power source 118 may also be a rechargeable battery that can be detached allowing for replacement. In the case of a rechargeable battery, a small built-in back-up battery (or super capacitor) can be provided for continuous power to be provided to patient monitor 102 during battery replacement. Communication between the components of patient monitor 102 in this example (may be established using an internal bus (not explicitly shown in FIG. 1).

Patient monitor 102 may be attached to one or more of several different types of sensors 104 and may be configured to measure and readout physiological data related to patient 106. As noted, sensors 104 may be attached to patient monitor 102 by conductive leads 120 which may be, for example, cables coupled to sensor interface 108. Additionally, or alternatively, one or more sensors 104 may connected to sensor interface 108 via a wireless connection. In which case sensor interface 108 may include circuitry for receiving data from and sending data to one or more devices using, for example, a WiFi® connection, a cellular network connection, and/or a Bluetooth® connection.

The data signals received from sensors 104, may be an analog signals. For example, the data signals for the ECG may be input to sensor interface 108, which can include an ECG data acquisition circuit (not shown separately in FIG. 1). An ECG data acquisition circuit may include amplifying and filtering circuitry as well as analog-to-digital (A/D) circuitry that converts the analog signal to a digital signal using amplification, filtering, and A/D conversion methods. In the event that the ECG sensor is a wireless sensor, sensor interface 108 may receive the data signals from a wireless communication module. Thus, sensor interface 108 is a component which may be configured to interface with one or more sensors 104 and receive sensor data therefrom.

As further described herein, the processing performed by an ECG data acquisition circuit may generate analog data waveforms or digital data waveforms that are analyzed by, in this particular embodiment, a microcontroller. However, other embodiments may use other kinds of processors. The microcontroller may be one of the processors 110.

The one or more processors 110, for example, may analyze the ECG waveforms to identify certain waveform characteristics and threshold levels indicative of conditions (abnormal and normal) of the patient 106 using one or more monitoring methods. A monitoring method may include comparing an analog or a digital waveform characteristic or an analog or digital value to one or more threshold values and generating a comparison result based thereon. The microcontroller may be, for example, a processor, an FPGA, an ASIC, a DSP, a microcontroller, or similar processing device.

The microcontroller may include a memory or use a separate memory 116. The memory may be, for example, a RAM, a memory buffer, a hard drive, a database, an EPROM, an EEPROM, a ROM, a flash memory, a hard disk, or any other non-transitory computer readable medium.

Memory 116 may store software or algorithms with executable instructions and the microcontroller may execute a set of instructions of the software or algorithms in association with executing different operations and functions of patient monitor 102 such as analyzing the digital data waveforms related to the data signals from sensors 104.

As noted, in the example of FIG. 1, conductive leads 120 between sensors 104 and sensor interface 108 may be an ECG lead set. Conductive leads 120 typically terminate at a sensor 104 that is attached to the patient for measuring ECG data.

As noted, an ECG signal reflects electrical impulses in the heart associated with the systolic rhythm of a beating heart.

A normal sinus rhythm includes a repeating succession of "heartbeats" corresponding to heart contractions, and an ECG signal may reflect various phases of such contractions.

FIG. 2 is a schematic representation of a "normal" sinus rhythm ECG wave 200. illustrates a sensed ECG signal corresponding to various phases of a single cardiac beat. As shown in FIG. 2, ECG wave 200 includes a plurality of distinct phases corresponding to periods of polarization and depolarization of regions of the cardiac muscle. In particular, ECG wave 200 includes a P-wave 202, a Q-wave 204, an R-wave 206 having a peak at a fiducial point 207, an S-wave 208, and a T-wave 210. Each of these waves represents either a positive or negative polarization relative to an ECG baseline 212.

A normal sinus rhythm ECG wave such as ECG wave 200 is commonly characterized according to a number of segments, including, as shown in FIG. 2, a P-R segment 214, a P-Q segment 216, a QRS complex 218, an S-T segment 220, and a Q-T segment 222. A normal sinus rhythm ECG wave such as ECG wave 200 may further be characterized by an "isoelectric point" (occurring at dashed line 215 in FIG. 2), an "onset" (occurring at dashed line 217 in FIG. 2), and a junction point or "J-point" 226. Referring to FIG. 2, J-point 226 in ECG wave 200 is the point where QRS complex 218 joins the S-T segment 220. J-point 226 represents the approximate end of depolarization and the beginning of repolarization. J-point 226 may deviate from baseline 212.

As noted above, noise and artifacts may be introduced into sensed ECG signals, such as baseline wander caused by motion of the patient or the leads, muscle/electromyographc ("EMG") artifacts, spectrum overlapping with the ECG signal, electrode motion artifacts, respiration artifacts, lead placement artifacts, and so on, which can cause the baseline (such as baseline 212 in FIG. 2) to vary. Variability of the ECG baseline can make it difficult to clinically assess a patient's ECG reading and reliably identify the various waves and segments, in the sensed ECG waveform.

Referring again to FIG. 1, the one or more processors 110 may further execute under programmed control processes for performing systolic segment measurements, such as S-T segment measurements, QRS-complex detection, and QRS-complex feature extraction. A QRS-complex is commonly the central and most visually obvious part of an ECG waveform, with a duration of approximately 80 milliseconds (mSec)-100 mSec in adults. Patient monitor 102 may identify the QRS-complex by, for example, identifying an R-wave within the QRS-complex. Processor(s) 110 may search one or more edge points of received sample signals, including a starting point, a peak point, a tail point, and an endpoint. By defining one or more edge points, processor(s) 110 may identify the R-wave and its corresponding QRS-complex.

Concurrently or subsequently, patient monitor 102 may further extract one or more features from the identified QRS-complexes, including but not limited to amplitude, width, morphology, curvature, symmetry, peak direction, segments of different waves including R-R segments (i.e., the time interval between two consecutive R-waves), P-R segments (time interval between the beginning of the upslope of the P wave to the beginning of QRS wave), and S-T segment measurements. Based on these extracted features, patient monitor 102 may further classify the QRS-complexes into different types referred to as "beats", including a normal beat or a bundle branch block beat (N), a ventricular ectopic beat (V), a supraventricular ectopic beat (S), a fusion of ventricular and normal beat (F) and a paced beat or a beat that cannot be classified (Q). Each beat type has its characteristic features and accordingly, physiological monitoring device 102 may store ECG template databases including various pre-determined threshold values or ranges of pre-determined threshold values for each feature. When a new QRS-complex is identified, patient monitor may extract one or more features and compare them with pre-determined threshold values or a ranges of threshold values, thereby classifying the QRS-complex into a specific beat type based on the comparison results.

In other examples, pre-determined threshold values or the ranges of threshold values may be dynamically updated. That is, after a new beat is classified, the extracted features of this beat are used to update the existing QRS-complex template database. When the identified QRS-complex and its corresponding classification indicate cardiac conditions, processor(s) 110 may generate alarms and display one or more extracted features for clinical providers. For example, the duration, amplitude, and morphology of the QRS-complex are useful for clinical providers to diagnose cardiac arrhythmias, conduction abnormalities, ventricular hyper-trophy, myocardial infarction, electrolyte derangements, and other cardiac conditions.

In clinical settings, artifact signals are often mixed with ECG signals, which makes it a challenge to systolic event identification, feature extraction, and subsequently, beat classification. For example, an artifact signal with a high amplitude and narrow width (e.g., high-frequency artifacts and low-frequency artifacts) may adversely impact the iden-tification of S-T segments, R-waves and subsequent feature extraction (e.g., R-R segment, P-R segment, R-wave ampli-tude, and S-T segment). On the other hand, baseline shift artifacts may corrupt the ECG signals and interfere with the identification and measurement of S-T segments, which are important diagnostic markers for ischemia and infarction.

S-T segment monitoring in particular may enable detec-tion of silent ischemia and result in changes in clinical management. Changes in the S-T segment may also add prognostic information that can potentially influence treat-ment decisions. Accurate measurement of the elevation of the S-T segment of an ECG waveform is important for detection of myocardial ischemia and infarction in a patient. Therefore, in various examples herein, S-T segment level measurement may be accurately performed in real time by updating an averaged ECG beat cycle waveform in a real time and reliable way, thereby accurately detecting systolic feature points such as J-points and onset points.

Figure 3A:
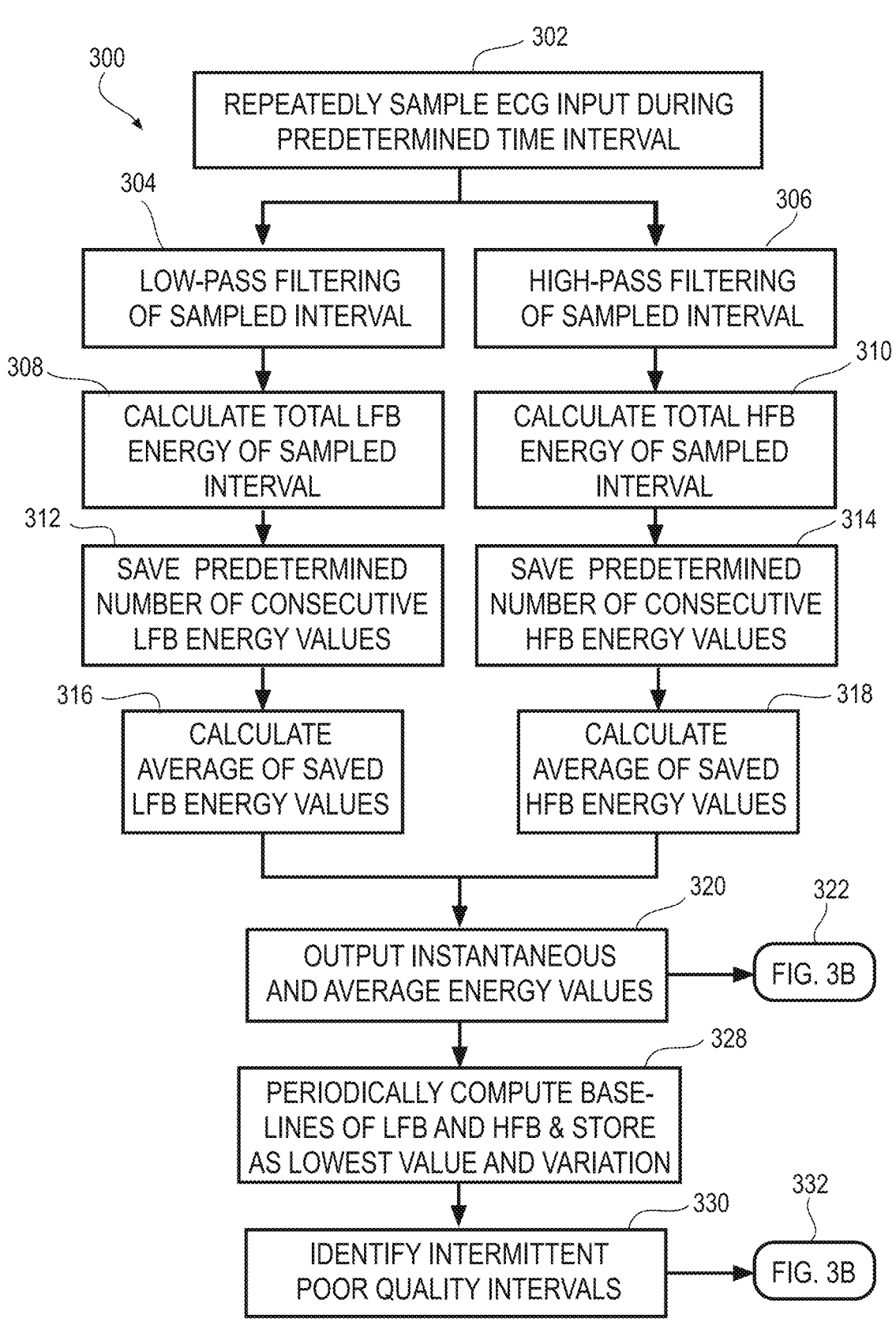
FIGS. 3A and 3B together comprise a flow diagram illustrating a method of processing ECG signals according to one or more examples.
Figure 3B:
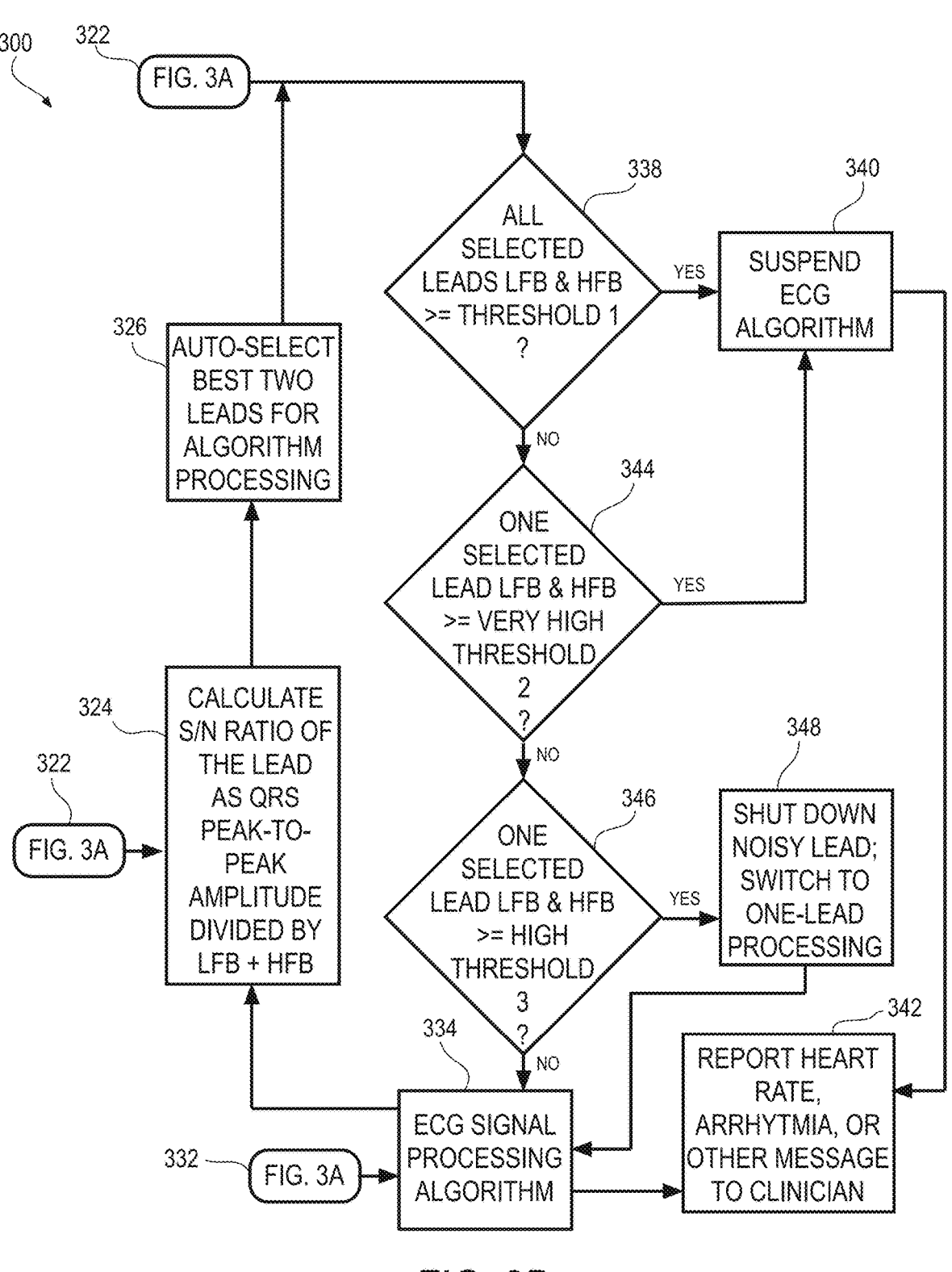

FIGS. 3A and 3B illustrate a method 300 for performing ECG signal processing according to one or more examples. Method 300 may be performed by patient monitor 102, and may be performed independently for each of multiple ECG leads associated with physiological monitoring system 100. The steps of method 300 depicted in FIGS. 3A and 3B may be performed in the digital realm, the analog realm, or a combination thereof.

As shown in FIG. 3A, method 300 begins at block 302 repeated sampling of the ECG signal on each ECG lead over a predetermined time interval. In examples, the ECG signal may be sampled 250 times per second over a 300 mSec interval, although different sampling rates and interval dura-tions may be specified. The acquired sampled waveform is subjected to low-pass filtering in block 304 and to high-pass filtering in block 306. The low-pass filtering (block 304) and the high-pass filtering (block 306) may be performed con-currently or sequentially depending on the embodiment. Furthermore, in each of the low-pass filtering (block 304) and the high-pass filtering (block 306), the signals may be filtered concurrently or sequentially depending on the embodiment. Either finite impulse response ("FIR") or infi-nite impulse response ("IIR") filters may be utilized. In examples, low-pass filtering may comprise filtering with a bandpass window of less and 1 Hz, and high-pass filtering may comprise filtering with a bandpass window higher than 20 Hz.

Thereafter, the total low-frequency bandpass ("LFB") energy is calculated in block 308, and the total high-frequency bandpass ("HFP") energy is calculated in block 310. The process of sampling the ECG input (block 302), low-pass filtering (block 304), and calculation of LFG and HFB energies (blocks 308 and 310, respectively) may be repeated continuously, such that, in block 312, a plurality of consecutive LFB energy values are stored in an array. For example, eight consecutive values, corresponding to 2.4 seconds of data, may be stored in block 312. Correspond-ingly, a plurality of consecutive HFB energy values are stored, in block 314.

In block 316, an average of the plurality of LFB energy values saved in block 312 is calculated, while in block 318, an average of the HFB energy values saved in block 314 is calculated. In block 320, the instantaneous LFB energy values and HFB energy values (from blocks 308 and 310, respectively), and the average LFB and HFB energy values (from blocks 316 and 318, respectively) are outputted. As shown by connecting block 322 in FIGS. 3A and 3B, these outputted values are used in block 324 to calculate a signal-to-noise ("S/N") ratio of the lead, by dividing the QRS peak-to-peak amplitude value divided by the sum of the LFB and HFB energy values.

Assuming that method 300 of FIGS. 3A and 3B is being performed independently on multiple leads, then as shown in FIG. 3B, in block 326 a selection is made of the best two leads to be utilized for further ECG processing according to the algorithm described in various examples herein. This selection in block 326 may be made based upon the signals having optimal S/N ratios, for example, S/N ratios greater than 10-12 db. as computed in block 324, for example. That is, in the illustrated example the "best" two leads will be those having the greatest S/N ratios. Other embodiments may use other measures for what is "best".

Referring again to FIG. 3A, method 300 may further involve, in block 328, periodically computing energy base-lines of the LFB and HFB energies. These baselines may be computed, for example, in terms of a lowest value and a variation value, i.e., a range of values, for each of the LFB and HFB energy values. The computation step of block 328 may be performed, for example, at 300 mSec intervals based on the past 10- to 20-seconds of averaged data from blocks 316 and 318.

In block 330, intermittent periods of poor ECG signal quality may be identified by comparing the LFB and HFB energy baselines computed in block 328. As shown by connecting block 332 in FIGS. 3A and 3B, this information regarding intermittent poor-quality intervals is provided to a block 334 for performing an ECG signal processing algo-rithm.

With continued reference to FIG. 3B, execution of the ECG processing algorithm according to one or more examples herein is based upon a selection of leads to be used for that purpose. The selection of leads begins with calcu-lation of S/N ratios for each lead, in block 324 as described above. In examples, the intermittent periods of poor ECG signal quality may be excluded from consideration by the ECG processing algorithm performed in block 334. The ECG algorithm is performed on the beats sensed on the ECG leads selected in block 326. Connecting block 322 in FIG.

3B reflects that the instantaneous and averaged energy values outputted from block 320 in FIG. 3A may be utilized in the assessment of ECG signals provided to the ECG signal processing algorithm (block 334) through a series of threshold assessments (blocks 338, 344, and 346) as herein described.

In particular, as the ECG signal processing algorithm is being performed in block 334, determinations are made, in decision block 338, whether all of the selected leads have LFB and HFB energies which are greater than or equal to a first predetermined threshold. If that is the case, then in block 340, the ECG algorithm is suspended, as this reflects a scenario where the ECG quality is insufficient to be relied upon for making clinical decisions. Upon suspension of the ECG algorithm in block 340, method 300 proceeds to block 342, in which the clinician may be advised of the patient's heart rate, an arrhythmia, S-T segment, or other message.

If all selected leads do not have LFB and HFB energies which exceed the first threshold in block 338, then a further determination is made, in block 344, whether at least one of the selected leads has LFB and HFB energy which exceeds a very high second predetermined threshold, in which case operation proceeds again to block 340, in which the ECG processing algorithm is suspended.

If neither selected lead has LFB and HFB energy exceeding the very high second threshold in decision block 344, then in decision block 346, a determination is made whether one of the selected lead has LFB and HFB energy exceeding a high third predetermined threshold. If not, the normal algorithm operation continues, beginning again at block 334. If one of the selected leads does have LFB and HFB energy exceeding the third high predetermined threshold (which may be lower than the very high first predetermined threshold, this signifies that the lead generating the signal is unsuitably noisy. In that case, in block 348, the noisy lead is shut down and one-lead operation is commenced. A report may be made from block 342 advising the clinician that one-lead operation has commenced.

In some examples, an ECG signal processing algorithm such as represented by block 324 in FIG. 3B may, among multiple processes, perform S-T segment measurements based upon the lead(s) selected as described herein with reference to FIGS. 3A and 3B. These measurements, or alerts based upon them, may be reported to the clinician in block 342 as shown in FIG. 3B. There are several challenges associated with accurate S-T segment measurement, including strong respiration artifacts in the sensed ECG signals, and baseline noise in the sensed ECG signals.

In cases of respiration artifacts in the sensed ECG signals, it is necessary to eliminate the artifact while preserving the low-frequency signal content especially important for S-T segment measurement, such as prescribed by industry standards such as promulgated by the Association for the Advancement of Medical Instrumentation (AAMI) and the International Electrotechnical Commission (IEC), particularly, IEC/AAMI Standard 60601 2-25.

The baseline noise including any respiration artifacts may be low-frequency signals (e.g., below 0.8-1.0 Hz). The frequency in an ECG signal is typically above 0.05 Hz. Thus, the frequency band of the baseline noise may overlap with the ECG signal of interest, such that a traditional finite impulse response (FIR) or infinite impulse response (IIF) high-pass filter with 0.05 Hz can meet the standard, but may not be sufficient to remove the baseline noise.

Accordingly, in some examples, filtering methodologies may be employed to remove baseline noise. One such methodology is disclosed in U.S. Pat. No. 9,480,411 to Zheng et al., entitled "Electrocardiogram Baseline Removal" ("the '411 patent") involves estimation of a baseline variation of the ECG signal from a filtered ECG signal and subtracting the estimated baseline variation from the original ECG to produce a baseline-removed ECG signal. The Zheng et al. '411 patent is hereby incorporated by reference herein in its entirety.

Furthermore, some professional recommendations, such as in the American Association of Critical Care Nurses (AACN) "Practice Alert of Ensuring Accurate ST-Segment Monitoring" suggest that clinicians perform further assessment (beyond baseline removal) in response to an S-T segment alarm indicating an S-T segment deviation lasting more than a full minute.

FIG. 4 is a flow diagram illustrating a method 400 for S-T segment measurement according to one or more examples. It is to be understood that the various steps depicted in FIG. 4 may be performed in a sequence other than that shown in FIG. 4. For example, some steps may be performed on an ongoing basis at the same time as other are being performed.

A first step 402 in method 400 is the removal of baseline noise from each incoming ECG signal of each selected lead. In examples, the selection of at least one lead and the baseline removal may be performed according to the method depicted in FIGS. 3A and 3B herein.

In step 404 of method 400, an "average beat" for each selected ECG lead is computed for a predetermined averaging interval. In one example, an average beat for an ECG lead is computed over a 15-second interval, an individual beat is included in creating an average beat over the 15-second averaging interval only if it is classified as normal or atrial-paced, and if it passes signal quality checks on the isoelectric point and S-T segment regions and the remaining qualified beats meet the minimum threshold. The averaging is accumulated and updated upon each incoming new beat, such that each beat is only $\frac{1}{8}^{th}$ weighted in the average beat, and the stored accumulated average beat is $\frac{7}{8}^{th}$ weighted.

In block 406 of method 400, the onset point (reference numeral 217 in FIG. 2) and the J-point (reference numeral 226 in FIG. 2) of the average beat computed in step 404 for each lead is identified. The isoelectric point (dashed line 215 in FIG. 2) may be determined relative to the onset point, e.g., a predetermined time before the onset point. To detect the onset point and J-point of the average beat, and arc-length curve algorithm may be employed.

In particular, The average beat for each lead is subjected to an arc length curve computation according to the following Equation (1):

$$\text{ArcL}[i] = \sum_{k=i-w}^{i} \sqrt{C + (\Delta y)_k^2} \qquad \text{Eq. (1)}$$

$$\Delta y_k = ecgwaveform[k] - ecgwaveform[k-1]$$

where i is the time index, C is a constant related to sample interval in mSec, w is the duration of the time window and should be approximately equal to the width of the widest QRS complex.

Figure 5A:
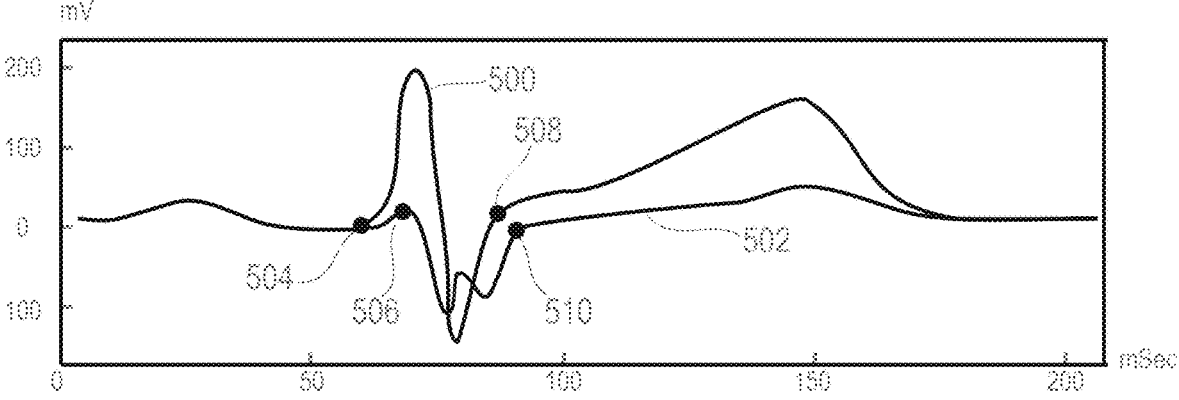
FIG. 5A illustrates a pair of sensed ECG signals before processing according to an ECG processing algorithm according to one or more examples.
Figure 5B:
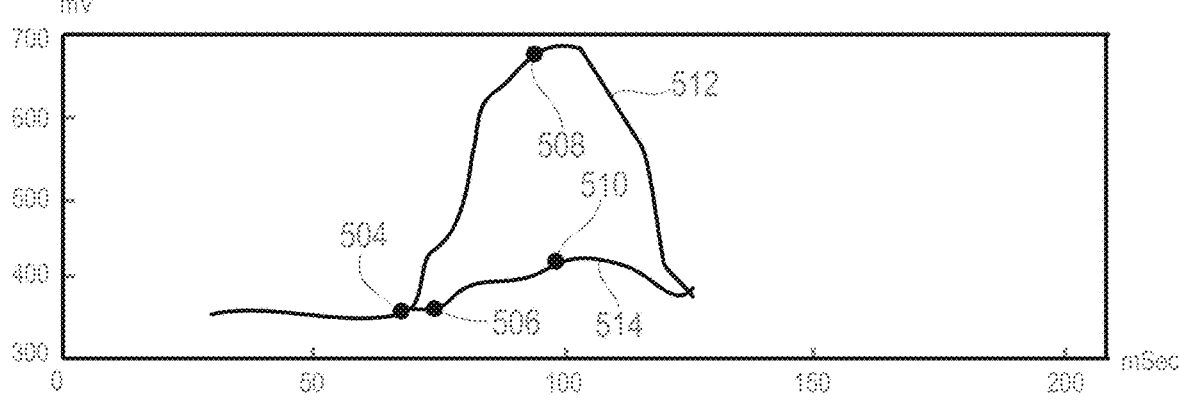
FIG. 5B illustrates a pair of sensed ECG signals after processing according to an ECG processing algorithm according to one or more examples.

FIGS. 5A and 5B illustrate how the arc-length curve algorithm reflected in Equation (1) above may be used to detect onset points and J-points on two independent leads. In FIG. 5A, a first averaged ECG signal 500 from a first lead and a second averaged ECG signal 502 from a second lead are shown. Reference numeral 504 identifies the onset point of averaged ECG signal 500 and reference numeral 506 identifies the onset point of averaged ECG signal 502. Reference numeral 508 identifies the J-point of averaged ECG signal 500, and reference numeral 510 identifies the J-point of averaged ECG signal 502. (It is to be noted that respective onset points 504 and 506 and respective J-points 508 and 510 are not synchronized on the two leads due to bundle branch block).

Computations according to Eq. (1) result in an arc-length curve 512 shown in FIG. 5B corresponding to averaged ECG signal 500 and an arc-length curve 514 shown in FIG. 5B corresponding to ECG signal 502. On the arc-length curves 512 and 514 of respective ECG signals 500 and 502, from a known R-point (fiducial point 207 in FIG. 2), the algorithm searches forward a predetermined time (e.g., 200 mSec) to identify the first point with maximum amplitude as the J-point. The algorithm then searches back from the identified J-point to the first point with minimum amplitude to identify the onset point.

With continued reference to FIG. 4, in block 408 the isoelectric point (dashed line 215 in FIG. 2) is determined relative to the identified onset point of the average beat (which ideally is the same for each beat in the averaging interval), In examples, the isoelectric point may be identified by assuming it to occur a predetermined time (e.g., 0.28 mSec) before the onset point. Also in block 408, the S-T segment of the average beat for each selected lead is computed, to provide an "interval complex measurement" for each selected lead during the averaging interval. In examples, the S-T measurement point is selected to be a predetermined interval relative to the J-point. For example, the S-T measurement point may be 20-, 40-, 60-, or 80-mSec from the J-point, depending upon the heart rate and/or selected by the user. The isoelectric point (reference numeral 215 I FIG. 2) is assumed to occur at a particular time (e.g., 0.28 mSec) before the onset point, and the S-T segment may be measured as the difference between the isoelectric point and the S-T measurement point for the average beat for each selected lead.

In block 410, the S-T segments of each beat from each selected lead, as computed in block 408, during the averaging interval are sorted, and upper and lower marginal measurements are discarded. In examples, the upper 25% and lower 25% of the computed S-T segments are discarded.

In block 412, for each selected lead, the S-T segments for each lead are averaged to produce, for each lead, an "each beat averaged measurement." Then, in block 414, for each lead, an average of the interval complex measurement computed in block 406 and the each eat averaged measurement is computed. These results may then be reported to the clinician, in block 342 from the flow diagram of FIG. 3B, at the end of each averaging interval.

Figure 6:
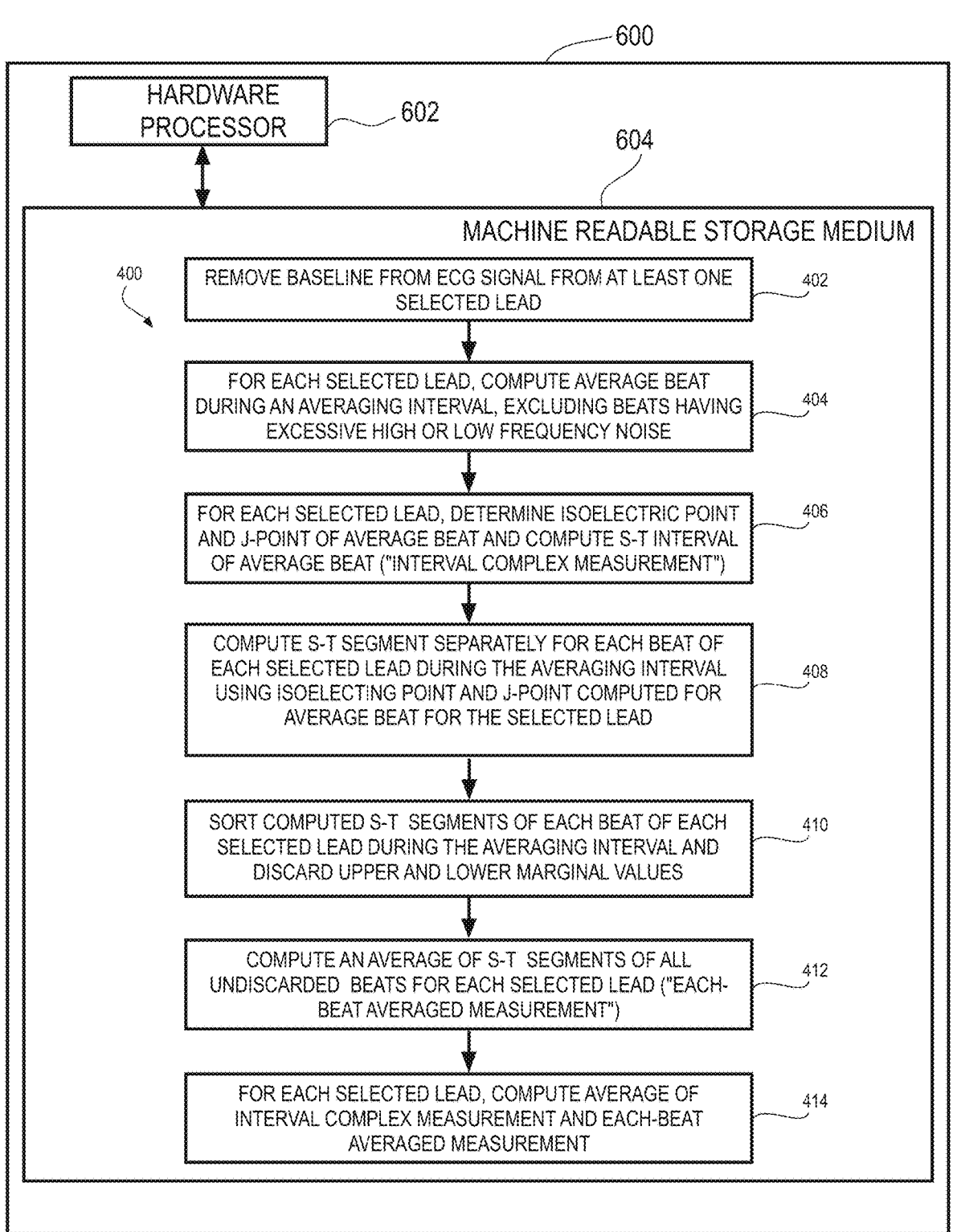
FIG. 6 is a block diagram of a computing resource implementing a method of operating a patient monitoring system according to one or more examples.

FIG. 6 is a block diagram representing a computing resource 600 implementing a method of ECG signal processing according to one or more examples. The computing resource 600 may be, for example and without limitation, a personal desktop computer (e.g., a personal computer), a mobile computing platform (e.g., a laptop or tablet), or a desktop computer accessing cloud computing resources. Computing resource 600 may include at least one hardware processor 602 and a non-transitory machine-readable storage medium 600. As illustrated, machine readable medium 604 may store instructions, that when executed by hardware processor 602 (either directly or via emulation/virtualization), cause hardware processor 602 to perform the method 400 of ECG signal processing described above with reference to FIG. 4.

In various examples, hardware processor 602 may be, for example and without limitation, a microcontroller, a central processing unit ("CPU"), a digital signal processor ("DSP"), a programmed logic array ("PLA"), or a custom processing circuit. Instructions may be executed by one or more processors, such as one or more central processing units ("CPU"), digital signal processors ("DSPs)", general purpose microprocessors, application specific integrated circuits ("ASICs"), field programmable logic arrays ("FP-GAs"), or other equivalent integrated or discrete logic circuitry. Accordingly, the term "processor," as used herein refers to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. A "controller," including one or more processors, may use electrical signals and digital algorithms to perform its receptive, analytic, and control functions, which may further include corrective functions. Thus, a controller is a specific type of processing circuitry, comprising one or more processors and memory, that implements control functions by way of generating control signals.

A computer-readable media may be any available media that may be accessed by a computer. By way of example, such computer-readable media may comprise random access memory ("RAM"), read-only memory ("ROM"), electrically-erasable/programmable read-only memory ("EE-PROM"), compact disc ROM ("CD-ROM") or other optical disk storage, magnetic disk storage or other magnetic storage devices, or any other medium that may be used to carry or store desired program code in the form of instructions or data structures and that may be accessed by a computer. Disk and disc, as used herein, includes compact disc ("CD"), laser disc, optical disc, digital versatile disc ("DVD"), floppy disk and Blu-ray® disc where disks usually reproduce data magnetically, while discs reproduce data optically with lasers.

Note also that the software implemented aspects of the subject matter hereof are usually encoded on some form of program storage medium or implemented over some type of transmission medium. The program storage medium is a non-transitory medium and may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The claimed subject matter is not limited by these aspects of any given implementation.

Accordingly, a first embodiment comprises a method of processing of electrocardiogram ("ECG") signals from a plurality of ECG leads connected to a patient. At least one lead is selected to provide an ECG signal from the patient; and for each of the selected leads, an average beat from a plurality of beats occurring during a predetermined averaging interval is computed. The onset point, isoelectric point, and the J-point of the average beat for each selected lead are computed, as well as an interval complex measurement reflecting an S-T segment of the average beat based on the determined isoelectric point and J-point.

Next, an S-T segment is computed separately for each beat on each lead during the averaging interval using the onset point and J-point of the average beat. These S-T segments are sorted, and upper and lower marginal values are discarded. The undiscarded S-T segments are averaged to compute an each beat averaged measurement. The each beat averaged measurement is averaged with the interval complex measurement, and the result is presented to a clinician.

In the method of the first embodiment, the baseline noise of the ECG signal on each selected lead is removed prior to further processing.

Further, in the method of the first embodiment, the averaging interval may be 15 seconds, although longer or shorter averaging intervals may be used.

Further, in the method of the first embodiment, determining the onset point and J-point of average beats comprises generating an arc-length curve function for the average beats.

Further, in the method of the first embodiment, determining the onset point and J-point of the average beat comprises generating an arc-length curve function for the average beats. The arc-length curve function may comprise:

$$ArcL[i] = \sum_{k=i-w}^{i} \sqrt{C + (\Delta y)_k^2}$$

$$\Delta y_k = ecgwaveform[k] - ecgwaveform[k-1]$$

where i is a time index, C is a constant related to sample interval in mSec, w is time window approximately equal to the width of the widest QRS complex during the predetermined period of time.

Further, in the method of the first embodiment, computing an average beat from a plurality of beats occurring during a predetermined averaging interval comprises updating the average beat on each incoming new beat such that each beat contributes a fractional weighting to the average beat. Still further, low-frequency and high-frequency noise measurements may be performed on the ECG signal on each selected lead and beats with low or high frequency noise exceeding a predetermined threshold are excluded from the computation of the average beat.

In a second embodiment, a physiological monitoring system for processing electrocardiogram ("ECG") signals from a plurality of ECG leads connected to a patient, includes at least one lead for providing an ECG signal from the patient. Signal processing circuitry coupled to each of the selected leads, and is configured to compute an average beat from a plurality of beats occurring during a predetermined averaging interval.

An onset point, isoelectric point and a J-point of the average beat are computed and used to compute an interval complex measurement reflecting an S-T segment of the average beat. Then, an S-T segment is computed separately for each beat during the averaging interval using the isoelectric point and the J-point of the average beat/These S-T segments are sorted, and S-T segments at upper and lower marginal values are discarded. An each beat averaged measurement comprising an average of undiscarded S-T segments is computed, and the each beat averaged measurement is averaged with the interval complex measurement. The result may then be reported to a clinician.

Further, in the second embodiment, the signal processing circuitry may remove baseline noise from the ECG signals from the at least one selected lead. The averaging interval is 15 seconds, although longer or shorter average intervals may be used.

Further, in the second embodiment, the onset point and J-point of the average beat are determined by generating an arc-length curve function for the average beats. The arc-length curve function may comprise:

$$ArcL[i] = \sum_{k=i-w}^{i} \sqrt{C + (\Delta y)_k^2}$$

$$\Delta y_k = ecgwaveform[k] - ecgwaveform[k-1]$$

where i is a time index, C is a constant related to sample interval in mSec. w is time window approximately equal to the width of the widest QRS complex during the predetermined period of time.

Further in the second embodiment, the signal processing circuitry computes an average beat from a plurality of beats occurring during a predetermined averaging interval by updating the average beat on each incoming new beat such that each beat contributes a fractional weighting to the average beat.

Further in the second embodiment, the signal processing circuitry performs low-frequency and high-frequency noise measurements of the ECG signal on each selected lead and excludes beats with low or high frequency noise exceeding a predetermined threshold from the computed average beat.

In a third embodiment, a computer-readable medium tangibly embodies instructions that, when executed by a processor, performs a method according to the first embodiment.

The detailed description is made with reference to the accompanying drawings and is provided to assist in a comprehensive understanding of various example embodiments of the present disclosure. Changes may be made in the function and arrangement of elements discussed without departing from the spirit and scope of the disclosure. Various embodiments may omit, substitute, or add various procedures or components as appropriate. For instance, features described with respect to certain embodiments may be combined in other embodiments. In addition, descriptions of well-known functions and constructions may be omitted for clarity and conciseness. Accordingly, those of ordinary skill in the art will recognize that various changes and modifications of the examples described herein can be made without departing from the spirit and scope of the present disclosure.

Use of the phrases "capable of," "capable to," "operable to," or "configured to" in one or more embodiments, refers to some apparatus, logic, hardware, and/or element designed in such a way to enable the use of the apparatus, logic, hardware, and/or element in a specified manner. Use of the phrase "exceed" in one or more embodiments, indicates that a measured value could be higher than a pre-determined threshold (e.g., an upper threshold), or lower than a pre-determined threshold (e.g., a lower threshold). When a pre-determined threshold range (defined by an upper threshold and a lower threshold) is used, the use of the phrase "exceed" in one or more embodiments could also indicate a measured value is outside the pre-determined threshold range (e.g., higher than the upper threshold or lower than the lower threshold). The subject matter of the present disclosure is provided as examples of apparatus, systems, methods, circuits, and programs for performing the features described in the present disclosure. However, further features or variations are contemplated in addition to the features described above. It is contemplated that the implementation of the components and functions of the present disclosure can be done with any newly arising technology that may replace any of the above-implemented technologies.

Various modifications to the disclosure will be readily apparent to those skilled in the art, and the generic principles defined herein may be applied to other variations without departing from the spirit or scope of the present disclosure. Throughout the present disclosure the terms "example," "examples," or "exemplary" indicate examples or instances and do not imply or require any preference for the noted examples. Thus, the present disclosure is not to be limited to the examples and designs described herein but is to be accorded the widest scope consistent with the principles and novel features disclosed.

What is claimed is:

1. A method of processing of electrocardiogram ("ECG") signals from a plurality of ECG leads connected to a patient, comprising:

selecting at least one lead to provide an ECG signal from the patient; and for each of the at least one selected leads:

computing an average beat from a plurality of beats occurring during a predetermined averaging interval;

determining an onset point and a J-point of the average beat;

computing an interval complex measurement reflecting an S-T segment of the average beat based on the determined onset point and J-point;

computing an isoelectric point of the average beat relative to the computed onset point;

computing an S-T segment separately for each beat during the averaging interval using the isoelectric point and J-point of the average beat;

sorting the computed S-T segments of each beat and discarding upper and lower marginal values;

computing an each beat averaged measurement comprising an average of undiscarded S-T segments;

computing an average of the interval complex measurement and the each beat averaged measurement; and reporting the computed average of the interval complex measurement and the each beat averaged measurement to a clinician.

2. The method of claim 1, further comprising removing baseline noise from each of the ECG signals from the at least one selected lead.

3. The method of claim 1, wherein the averaging interval is 15 seconds.

4. The method of claim 1, wherein determining the onset point and J-point of the average beat comprises generating an arc-length curve function for the average beats.

5. The method of claim 4, wherein the arc-length curve function comprises:

$$\mathrm{Arc}L[i] = \sum_{k=i-w}^{i} \sqrt{C + (\Delta y)_k^2}$$

$$\Delta y_k = ecgwaveform[k] - ecgwaveform[k-1]$$

where i is a time index, C is a constant related to sample interval in mSec, w is time window approximately equal to the width of the widest QRS complex during the predetermined period of time.

6. The method of claim 1, wherein computing an average beat from a plurality of beats occurring during a predetermined averaging interval comprises updating the average beat on each incoming new beat such that each beat contributes a fractional weighting to the average beat.

7. The method of claim 1, further comprising performing low-frequency and high-frequency noise measurements of the ECG signal on each selected lead and excluding beats with low or high frequency noise exceeding a predetermined threshold.

8. A physiological monitoring system for processing electrocardiogram ("ECG") signals from a plurality of ECG leads connected to a patient, comprising:

at least one lead for providing an ECG signal from the patient;

signal processing circuitry coupled to each of the at least one selected leads, the signal processing circuitry configured to:

compute an average beat from a plurality of beats occurring during a predetermined averaging interval;

determine an onset point and a J-point of the average beat;

computing an isoelectric point of the average beat relative to the onset point;

compute an interval complex measurement reflecting an S-T segment of the average beat based on the determined isoelectric point and J-point;

compute an S-T segment separately for each beat during the averaging interval using the onset point and the J-point of the average beat;

sort the computed S-T segments of each beat and discarding upper and lower marginal values;

compute an each beat averaged measurement comprising an average of undiscarded S-T segments;

compute an average of the interval complex measurement and the each beat averaged measurement; and report the computed average of the interval complex measurement and the each beat averaged measurement to a clinician.

9. The system of claim 8, wherein the signal processing circuitry removes baseline noise from the ECG signals from the at least one selected lead.

10. The system of claim 8, wherein the averaging interval is 15 seconds.

11. The system of claim 8, wherein the signal processing circuitry determines the onset point and J-point of the average beat by generating an arc-length curve function for the average beats.

12. The system of claim 11, wherein the arc-length curve function comprises:

$$\mathrm{Arc}L[i] = \sum_{k=i-w}^{i} \sqrt{C + (\Delta y)_k^2}$$

$$\Delta y_k = ecgwaveform[k] - ecgwaveform[k-1]$$

where i is a time index, C is a constant related to sample interval in mSec, w is time window approximately equal to the width of the widest QRS complex during the predetermined period of time.

13. The system of claim 8, wherein the signal processing circuitry computes an average beat from a plurality of beats occurring during a predetermined averaging interval by updating the average beat on each incoming new beat such that each beat contributes a fractional weighting to the average beat.

14. The system of claim 8, wherein the signal processing circuitry performs low-frequency and high-frequency noise measurements of the ECG signal on each selected lead and excludes beats with low or high frequency noise exceeding a predetermined threshold from the computed average beat.

15. A computer-readable medium tangibly embodying instructions that, when executed by a processor, performs a method of processing of electrocardiogram ("ECG") signals from a plurality of ECG leads connected to a patient, comprising:

selecting at least one lead to provide an ECG signal from the patient;

for each of the at least one selected leads:

computing an average beat from a plurality of beats occurring during a predetermined averaging interval;

determining an onset point and a J-point of the average beat;

computing an isoelectric point of the average beat relative to the onset point;

computing an interval complex measurement reflecting an S-T segment of the average beat based on the determined isoelectric point and J-point;

computing an S-T segment separately for each beat during the averaging interval using the onset point and J-point of the average beat;

sorting the computed S-T segments of each beat and discarding upper and lower marginal values;

computing an each beat averaged measurement comprising an average of undiscarded S-T segments;

computing an average of the interval complex measurement and the each beat averaged measurement; and reporting the computed average of the interval complex measurement and the each beat averaged measurement to a clinician.

16. The computer-readable medium of claim 15, wherein the method further comprises removing baseline noise from the ECG signals from the at least one selected lead.

17. The computer-readable medium of claim 15, wherein the averaging interval is 15 seconds.

18. The computer-readable medium of claim 15, wherein determining the onset point and J-point of the average beat comprises generating an arc-length curve function for the average beats.

19. The computer-readable medium of claim 18, wherein the arc-length curve function comprises:

$$\text{Arc}L[i] = \sum_{k=i-w}^{i} \sqrt{C + (\Delta y)_k^2}$$

$$\Delta y_k = ecgwaveform[k] - ecgwaveform[k-1]$$

where i is a time index, C is a constant related to sample interval in mSec, w is time window approximately equal to the width of the widest QRS complex during the predetermined period of time.

20. The computer-readable medium of claim 15, wherein computing an average beat from a plurality of beats occurring during a predetermined averaging interval comprises updating the average beat on each incoming new beat such that each beat contributes a fractional weighting to the average beat.

* * * * *